United States Patent
Yan et al.

(10) Patent No.: US 12,023,142 B2
(45) Date of Patent: Jul. 2, 2024

(54) FEEDBACK-TYPE INTELLIGENT SYRINGE

(71) Applicant: SINONEEDLE INTELLIGENCE TECHNOLOGY CO., LTD., Hubei (CN)

(72) Inventors: Zibao Yan, Hubei (CN); Liuqing Chen, Hubei (CN); Chaoyang Dong, Hubei (CN); Pengfei Chen, Hubei (CN); Quan Liu, Hubei (CN); Bo Yin, Hubei (CN)

(73) Assignee: SINONEEDLE INTELLIGENCE TECHNOLOGY CO., LTD. (CN)

( * ) Notice: Subject to any disclaimer, the term of this patent is extended or adjusted under 35 U.S.C. 154(b) by 198 days.

(21) Appl. No.: 17/267,793

(22) PCT Filed: Aug. 21, 2020

(86) PCT No.: PCT/CN2020/110611
§ 371 (c)(1),
(2) Date: Feb. 10, 2021

(87) PCT Pub. No.: WO2021/043011
PCT Pub. Date: Mar. 11, 2021

(65) Prior Publication Data
US 2022/0369946 A1    Nov. 24, 2022

(30) Foreign Application Priority Data
Sep. 4, 2019    (CN) .......................... 201910832459.0

(51) Int. Cl.
*A61B 5/053* (2021.01)
*A61M 5/178* (2006.01)

(52) U.S. Cl.
CPC ............. *A61B 5/053* (2013.01); *A61M 5/178* (2013.01)

(58) Field of Classification Search
CPC ....... A61B 5/053; A61B 5/0538; A61B 5/063; A61B 5/4887; A61M 5/178; A61M 5/3286; A61M 5/329; A61M 5/427; A61M 1/0023; A61M 1/73; A61M 5/32; A61M 5/3287; A61M 2230/65
See application file for complete search history.

(56) References Cited

U.S. PATENT DOCUMENTS

| | | | |
|---|---|---|---|
| 4,940,060 A * | 7/1990 | Gu | A61H 39/02 600/548 |
| 6,845,264 B1 * | 1/2005 | Skladnev | A61B 5/0531 600/407 |
| 7,580,743 B2 * | 8/2009 | Bourlion | A61B 5/053 606/80 |

(Continued)

FOREIGN PATENT DOCUMENTS

| | | | | |
|---|---|---|---|---|
| EP | 3181037 A1 * | 6/2017 | ......... | A61B 5/14503 |
| WO | WO-2009019707 A1 * | 2/2009 | ......... | A61B 17/3401 |
| WO | WO-2009083651 A1 * | 7/2009 | ............. | A61B 5/053 |

*Primary Examiner* — Eric F Winakur
*Assistant Examiner* — Abel Seifu Abegaz

(57) ABSTRACT

A feedback-type intelligent syringe is provided, which includes a syringe needle and a needle seat, the syringe needle is provided with a first electrode and a second electrode for detecting impedance of a human tissue, the first electrode and the second electrode are electrically connected with a main control device, and the main control device is electrically connected with a displayer or a reminding device.

7 Claims, 10 Drawing Sheets

(56) References Cited

U.S. PATENT DOCUMENTS

| | | | |
|---|---|---|---|
| 2003/0216663 A1* | 11/2003 | Jersey-Willuhn | A61B 5/412 977/932 |
| 2014/0039481 A1* | 2/2014 | Coe | A61B 18/14 606/41 |
| 2014/0276573 A1* | 9/2014 | Miesel | A61M 5/46 604/506 |
| 2016/0081585 A1* | 3/2016 | Halter | A61B 10/0233 29/605 |

* cited by examiner

FEEDBACK-TYPE INTELLIGENT SYRINGE

FIELD

The present invention relates to the field of medical instruments, and more particularly, to a feedback-type intelligent syringe.

BACKGROUND

Injection and suction positions are manually judged during use of an existing syringe, which depends on long-term training of medical staffs, but even skilled medical staffs are difficult to ensure that a syringe needle can be located at a predetermined position every time. Firstly, in operations involving suction, such as arterial blood, tumor dropsy, cerebrospinal fluid, adipose tissue, and the like, some operations need to be completed under helps of other auxiliary devices, such as a bedside CT machine, and the like. Secondly, surrounding tissues are rapidly necrotic after embolism due to injection of fillers into blood vessels every year when many doctors inject the fillers into a human body, resulting in major medical accidents which cannot be scientifically avoided. Sometimes target administration cannot be accurately performed in place, resulting in a discount on a treatment effect. A feedback-type syringe technology may make up for such defect, thus providing intelligent eyes for doctors around the world to inject and extract, and providing accurate tools for treat lesions of patients. The Chinese patent document CN205163829U records a full-automatic injection device for automatically scanning a blood vessel, which scans a three-dimensional image of a blood vessel in a human body part through a set blood vessel scanner, but a structure and a specific workflow of the blood vessel scanner are not described in detail in the document. The Chinese patent document CN101564294A records a method for structural information fused electrical impedance tomography, and gives a technical solution for obtaining human tissue imaging by detecting electrical resistance of an internal tissue of an organism based on an electrode, but the solution is complex in structure and application, which limits a clinical use value.

SUMMARY

The technical problem to be solved by the present invention is to provide a feedback-type intelligent syringe and a method thereof, which can quickly and accurately detect and position impedance of skin, muscle, body fluid, and blood, and can perform intelligent injection or suction according to a change of the impedance.

In order to solve the above technical problem, the technical solution used in the present invention is that: a feedback-type intelligent syringe includes a syringe needle and a needle seat, wherein the syringe needle is provided with a first electrode and a second electrode for detecting impedance of a human tissue, the first electrode and the second electrode are electrically connected with a main control device, and the main control device is electrically connected with a displayer or a reminding device.

In a preferred solution, the syringe needle is made of an insulating material or a metal material, and an outer layer of the syringe needle is coated with an inner insulating layer; the first electrode and the second electrode are arranged along a length direction of the syringe needle; and out layers of the first electrode and the second electrode are coated with outer insulating layers, and one ends of the first electrode and the second electrode are only exposed at positions close to a tip.

In a preferred solution, the other ends of the first electrode and the second electrode extend to an outer wall of the needle seat, the main control device is sleeved with the needle seat, an inner wall of the main control device is provided with a first lead-in electrode and a second lead-in electrode, and the first lead-in electrode and the second lead-in electrode are electrically connected with the first electrode and the second electrode respectively.

In a preferred solution, in the main control device, a main control system is electrically connected with a reference signal source, the reference signal source is electrically connected with a band-pass filter, the band-pass filter is electrically connected with the micro-signal amplification circuit, and the micro-signal amplification circuit is electrically connected with the first electrode and the second electrode.

A current detection circuit is electrically connected with the second electrode.

In a preferred solution, the micro-signal amplification circuit is an instrument amplifier circuit.

A reference signal passes through an output end of the band-pass filter, and is amplified and modulated by signal control, and then electrically connected with one input of the micro-signal amplification circuit and the first electrode directly.

The other input of the micro-signal amplification circuit is electrically connected with the second electrode and the current detection circuit.

In a preferred solution, a structure of the main control device is that: the main control system is electrically connected with the reference signal source, the reference signal source is electrically connected with the band-pass filter, and after the reference signal passes through the band-pass filter, a detection current is provided for the first electrode and the second electrode through a signal control module.

The first electrode and the second electrode are electrically connected with the micro-signal amplification circuit and the current detection circuit respectively, the micro-signal amplification circuit and the current detection circuit are electrically connected with at least two sets of A/D conversion modules respectively, the A/D conversion modules are electrically connected with a digital signal processing module, and the digital signal processing module is electrically connected with the main control system.

In a preferred solution, a third electrode is also arranged at a position of the needle seat, the third electrode is used for reliable contact with skin, the third electrode is electrically connected with the main control device through a micro-signal amplification circuit, the third electrode is rotatably connected with the needle seat, and the third electrode and one of the first electrode and the second electrode form a frequency conversion impedance detection circuit.

In a preferred solution, the needle seat is also provided with an array electrode, the array electrode is electrically connected with the main control device through the micro-signal amplification circuit, and the array electrode and one of the first electrode and the second electrode form the frequency conversion impedance detection circuit.

In a preferred solution, a plurality of array electrodes are provided, the plurality of array electrodes are arranged on a flexible fixing belt, and the flexible fixing belt is provided with an adhesive or a gluing buckle with ends connected with each other, so that the array electrodes are able to reliably contact with the skin, and positions of muscles and blood vessels are judged outside the skin.

In a preferred solution, a low frequency current signal of 0 Hz to 100 Hz is connected between the first electrode and the second electrode to determine a position of the tip of the syringe needle; a medium and low frequency signal of 100 Hz to 50 k Hz is connected between one of the first electrode and the second electrode, and the third electrode or the array electrode for scanning different tissues of a human body; a switching circuit is also provided for switching the low frequency current signal and the medium and low frequency signal; and the displayer or the reminding device includes a display screen, an LED indicator light, or a buzzer.

The present invention provides a feedback-type intelligent syringe, impedance of tissues and organs including skin, muscle, dropsy, blood, and the like can be accurately measured by using the above structure, so that a basis is provided for intelligent injection and extraction. In the present invention, double detection manners including the direct current and the medium and low frequency microcurrent are used, accurate detection and flexible setting are performed according to a change of the impedance of the tissues such as fat, muscle, body fluid, blood, spinal fluid, and the like, so that the syringe needle easily and accurately detects an injection site or an extracted tissue, and meanwhile, a reconstructed image is restored or a prompt is given through a specific algorithm, so that injection or extraction is more accurate. For example, damages including malposition, embolism, and the like during injection are avoided, and medicine is accurately administrated; or accurate monitoring is performed during fat extraction, so that a damage caused by wrong extraction is avoided; or when a tumor dropsy and a cerebrospinal fluid are extracted, a medical risk is reduced through accurate scanning and prediction, and accurate positioning, and a treatment efficiency of a doctor is greatly improved.

BRIEF DESCRIPTION OF THE DRAWINGS

The present invention is further described hereinafter with reference to the accompanying drawings and the embodiments.

Figure 1:
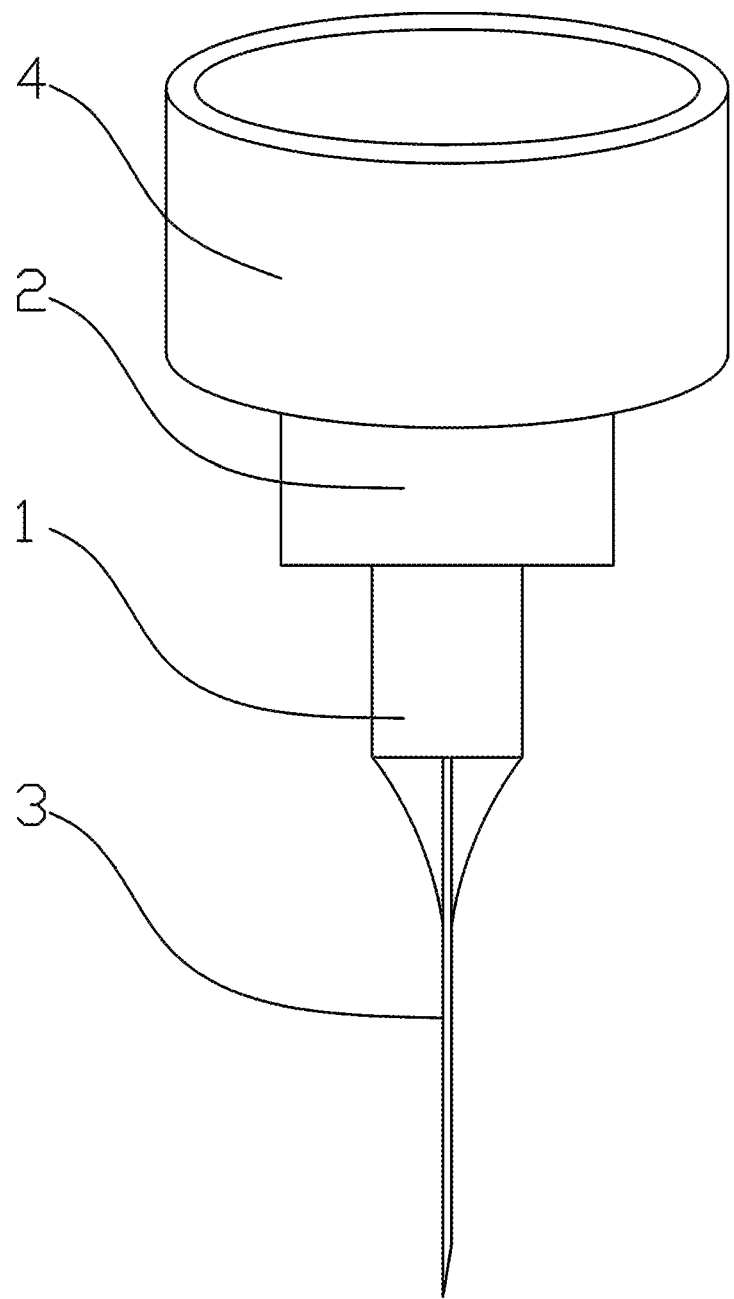
FIG. 1 is a schematic diagram of a structure of the present invention.

In the drawings: 1 refers to needle seat, 2 refers to main control device, 3 refers to syringe needle, 31 refers to inner insulating layer, 4 refers to syringe cylinder, 5 refers to first electrode, 6 refers to second electrode, 7 refers to third electrode, 8 refers to array electrode, 9 refers to flexible fixing band, 10 refers to skin, 11 refers to arterial blood vessel, 12 refers to outer insulating layer, 13 refers to first lead-in electrode, 14 refers to second lead-in electrode, 15 refers to detected tissue equivalent circuit, and OP3 refers to current detection circuit.

DETAILED DESCRIPTION

Embodiment 1

As shown in FIG. 1 to FIG. 7, a feedback-type intelligent syringe includes a syringe needle 3 and a needle seat 1. The syringe needle 3 is provided with a first electrode 5 and a second electrode 6 for detecting impedance of a human tissue, the first electrode 5 and the second electrode 6 are electrically connected with a main control device 2, and the main control device 2 is electrically connected with a displayer or a reminding device. With the structure, electrical signals are connected to the first electrode 5 and the second electrode 6 through the main control device 2, so that a specific position where a tip is located on the human tissue is judged according to the impedance.

After detection, a direct current resistivity (Ω·m) of the human tissue is as follows:

cerebrospinal fluid: 0.555; serum: 0.714; blood: 1.85; nerve: 25.0; liver: 80.0; muscle: 90.0; brain: 107; fat: $10.8 \times 10^2$; wet skin: $38.0 \times 10^2$; dry skin: $40.0 \times 10^3$; and membraneless bone: $20 \times 10^5$.

In the example, a position where the tip is located on a human body may be accurately judged by connecting a direct current. The solution has a high application value during blood or body fluid suction, such as arterial blood collection, and lymph, cerebrospinal fluid and tumor dropsy extraction.

Figure 2:
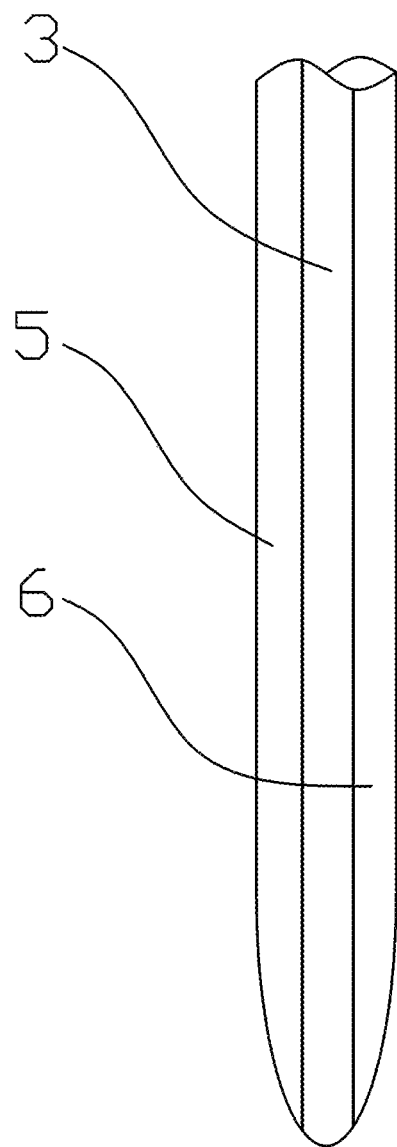
FIG. 2 is a schematic diagram of a structure of a syringe needle in the present invention.
Figure 3:
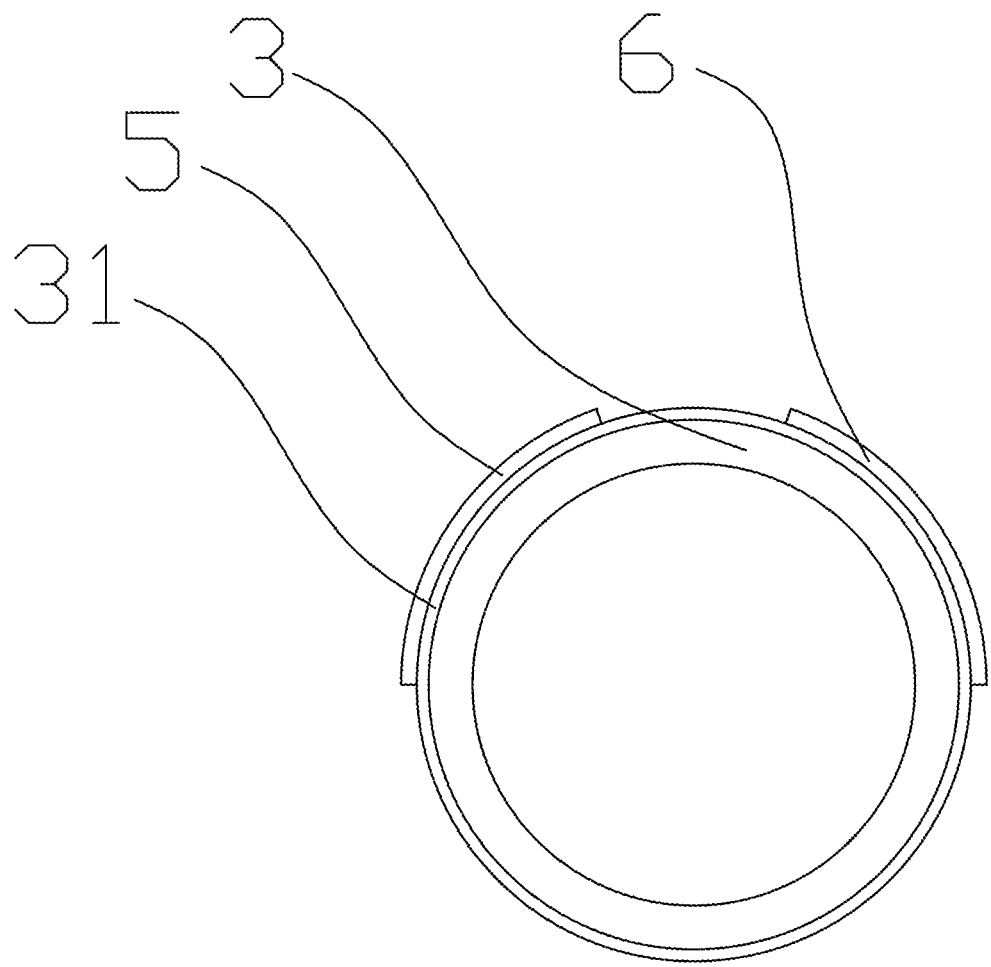
FIG. 3 is a schematic diagram of a cross-section of the syringe needle in the present invention.
Figure 6:
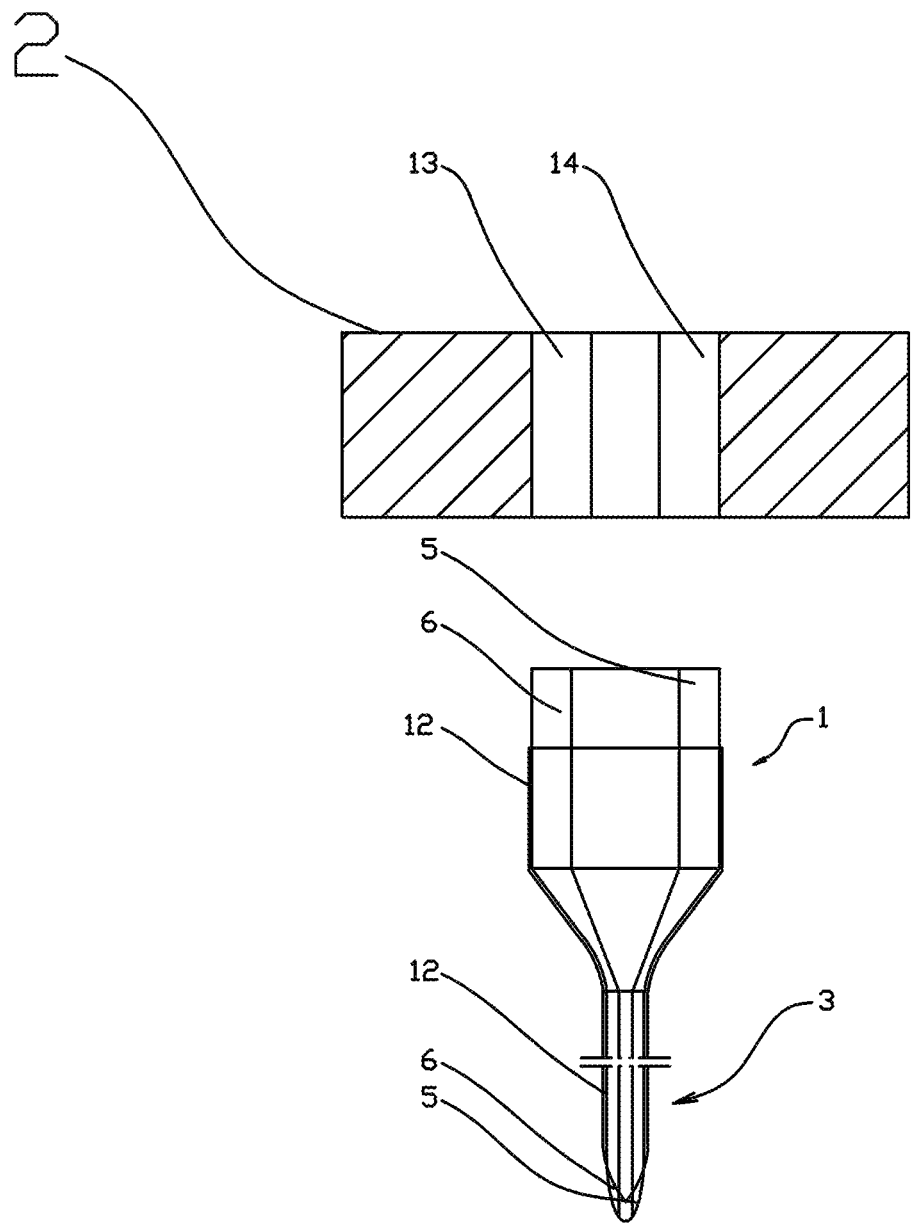
FIG. 6 is a schematic diagram of a connecting structure of a main control device and a needle seat in the present invention.

The preferred solution is shown in FIG. 2, FIG. 3, and FIG. 6. The syringe needle 3 is made of an insulating material, such as an insulating material made of alumina ceramic, and then a biocompatible coating is coated on a surface of aluminium oxide ceramic. Or, the syringe needle is made of a flexible glass material, and then a polymer film with a biocompatibility is coated on a surface of flexible glass. Insulating layers may be, for example, a silk fibroin film, polyvinylpyrrolidone, quaternary ammonium salt, Teflon, and a heparin compound, and other coatings generated by physical vapor deposition (PVD) and chemical vapor deposition (CVD).

Or, the syringe needle 3 is made of a metal material, an outer layer of the syringe needle 3 is coated with an inner insulating layer 31, and an insulating layer with a biocompatibility is used as the inner insulating layer 31.

The first electrode 5 and the second electrode 6 are arrange along a length direction of the syringe needle 3.

A preferred solution is shown in FIG. 6, out layers of the first electrode 5 and the second electrode 6 are coated with outer insulating layers 12, and one ends of the first electrode 5 and the second electrode 6 are only exposed at positions close to a tip. The structure ensures that only a position of the tip can conduct a current to a tissue contacted by the tip, while other positions are insulated, so that a detection result of the position of the tip cannot be interfered, thus improving an accuracy of human tissue detection.

A preferred solution is shown in FIG. 6, the other ends of the first electrode 5 and the second electrode 6 extend to an outer wall of the needle seat 1, the main control device 2 is sleeved with the needle seat 1, an inner wall of the main control device 2 is provided with a first lead-in electrode 13 and a second lead-in electrode 14, and the first lead-in electrode 13 and the second lead-in electrode 14 are electrically connected with the first electrode 5 and the second electrode 6 respectively. Further preferably, a flexible electrode structure is used in the first lead-in electrode 13 and the second lead-in electrode 14. When the main control device 2 is sleeved with the needle seat 1, the first lead-in electrode 13 is connected with the first electrode 5, and the second lead-in electrode 14 is connected with the second electrode 6. An expensive part of the main control device 2 can be reused through disassembly by using the structure that the main control device 2 is sleeved with the needle seat 1, and it is acceptable to increase costs of the first electrode 5 and the second electrode 6 only by plating on the syringe needle 3.

Figure 9:
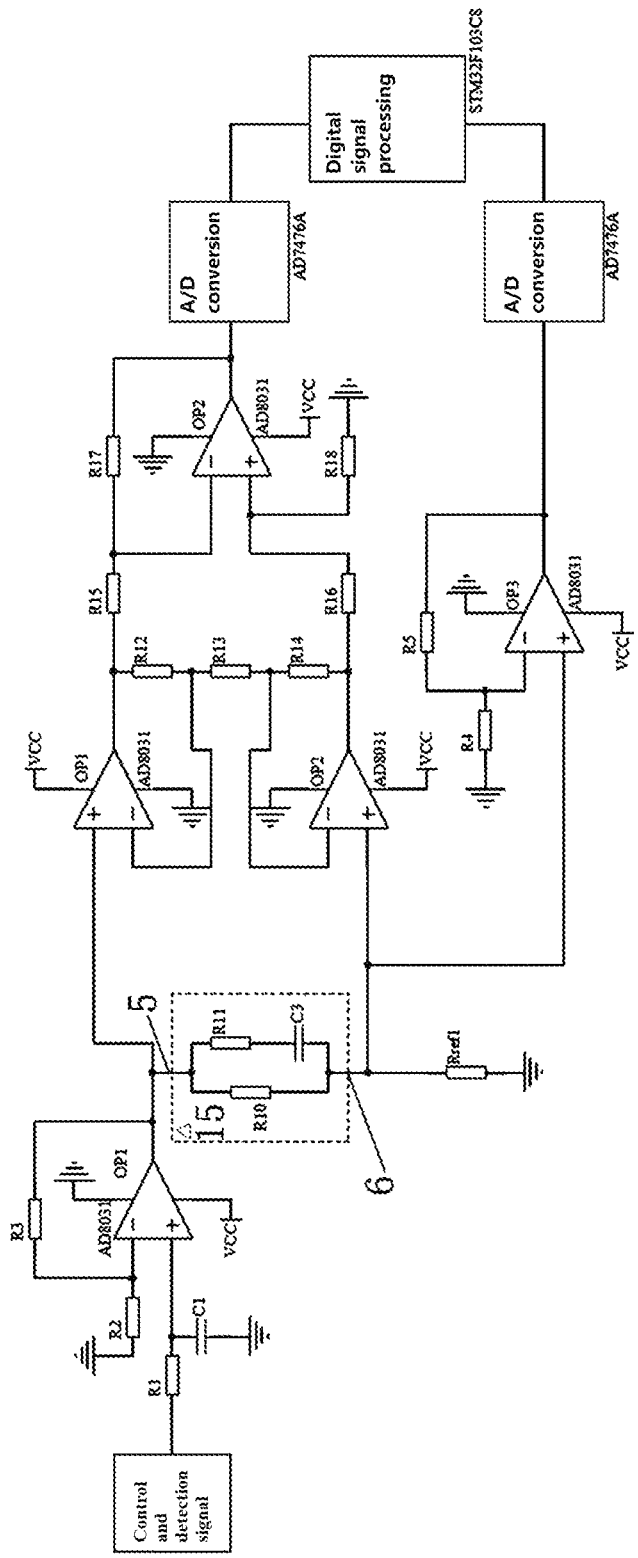
FIG. 9 is a schematic diagram of a micro-signal amplification circuit in the present invention.
Figure 10:
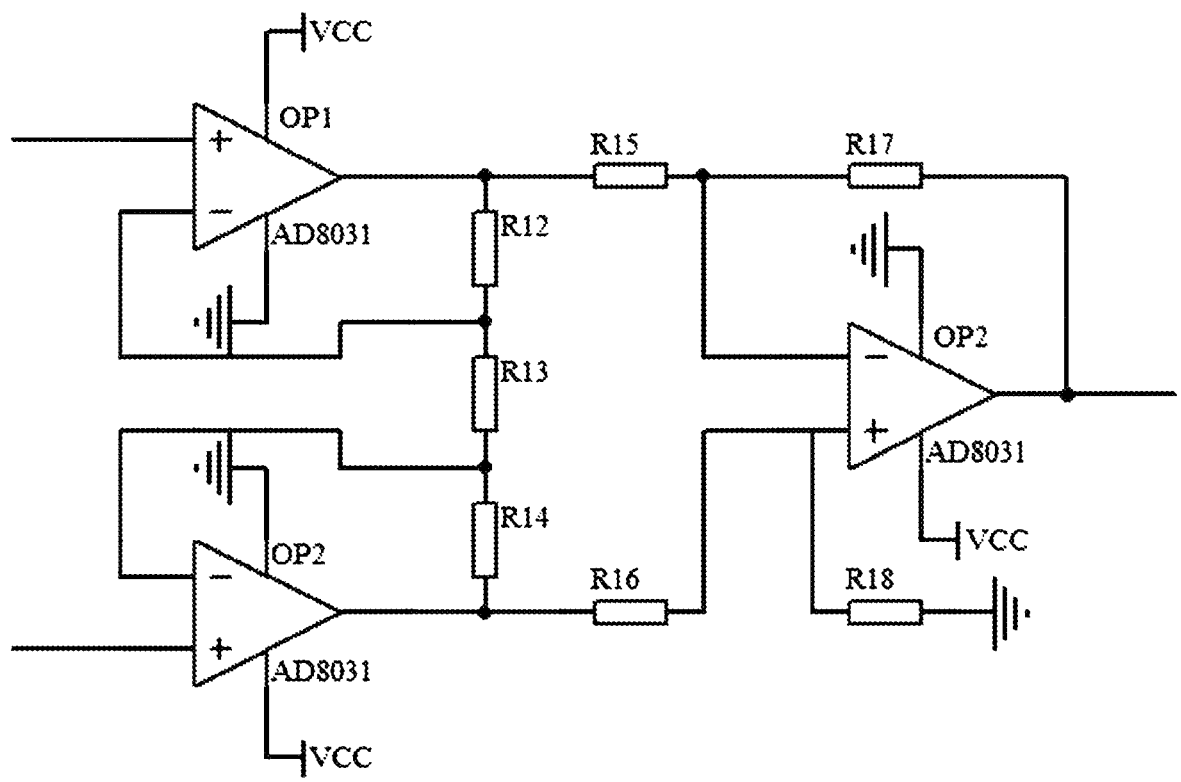
FIG. 10 is a schematic diagram of a human impedance detection circuit in the present invention.

A preferred solution is shown in FIG. 9, in the main control device 2, a main control system is electrically connected with a reference signal source, the reference signal source is electrically connected with a band-pass filter, the band-pass filter is electrically connected with the micro-signal amplification circuit, and the micro-signal amplification circuit is electrically connected with the first electrode 5 and the second electrode 6.

A current detection circuit OP3 is electrically connected with the second electrode 6. A dashed box in FIG. 9 represents a detected tissue equivalent circuit 15.

In a preferred solution, the micro-signal amplification circuit is an instrument amplifier circuit.

A reference signal source passes through an output end of the band-pass filter, and is amplified and modulated by signal control, and then electrically connected with one input of the micro-signal amplification circuit and the first electrode 5 directly.

The other input of the micro-signal amplification circuit is electrically connected with the second electrode 6 and the current detection circuit OP3.

In a preferred solution, a structure of the main control device 2 is that: the main control system is electrically connected with the reference signal source, the reference signal source is electrically connected with the band-pass filter, and after the signal passes through the band-pass filter, a detection current is provided for the first electrode 5 and the second electrode 6 through a signal control module.

The first electrode 5 and the second electrode 6 are electrically connected with the micro-signal amplification circuit and the current detection circuit respectively, the micro-signal amplification circuit and the current detection circuit are electrically connected with at least two sets of A/D conversion modules respectively, the A/D conversion modules are electrically connected with a digital signal processing module, and the digital signal processing module is electrically connected with the main control system. In the example, an embedded processor stm32f103c8 is used as the digital signal processing module, and an AD7476 is used as the A/D conversion module. An intel or ARM series CPU is used in the main control system.

Embodiment 2

Figure 4:
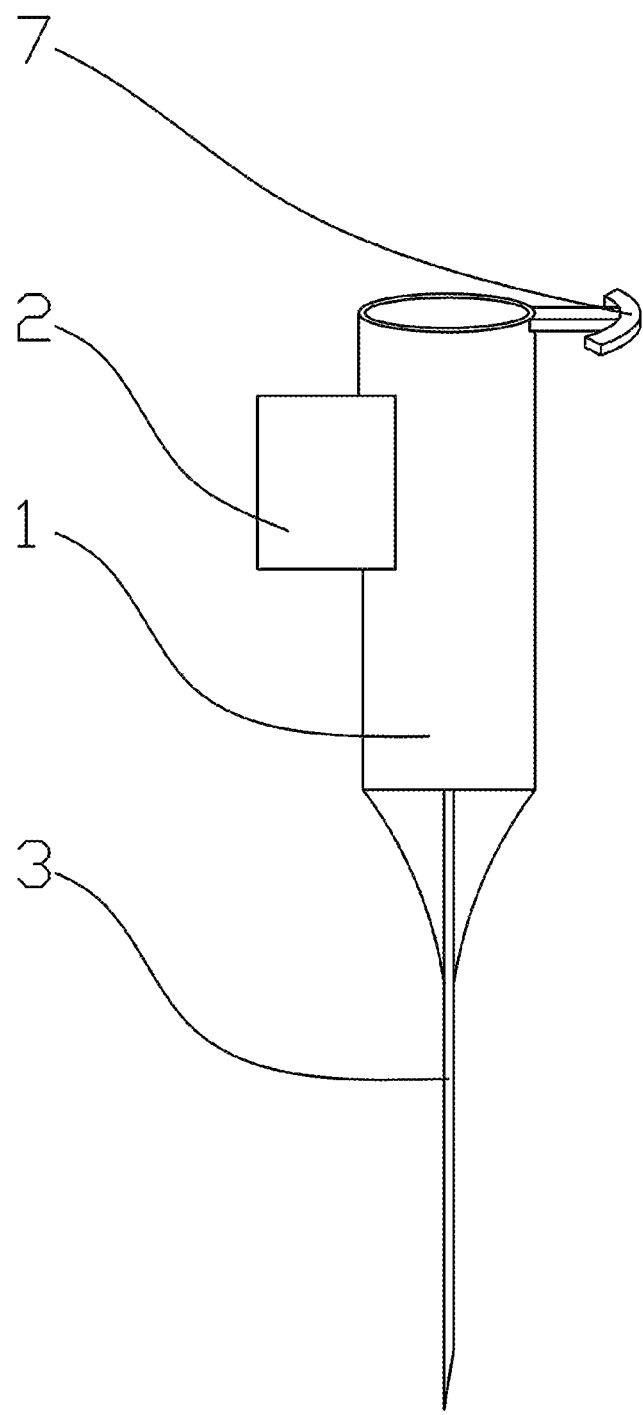
FIG. 4 is a schematic diagram of another preferred structure in the present invention.

Based on the Embodiment 1, a preferred solution is shown in FIG. 4, a third electrode 7 is also arranged at a position of the needle seat 1, the third electrode 7 is electrically connected with the main control device 2 through a micro-signal amplification circuit, the third electrode 7 is rotatably connected with the needle seat 1, and the third electrode 7 and one of the first electrode 5 and the second electrode 6 form a frequency conversion impedance detection circuit. A direction of the syringe needle 3 is rotated with the third electrode 7 as a center, the third electrode 7 and the first electrode 5 or the second electrode 6 on the syringe needle 3 both reliably contact with skin, and an alternating current is given between the third electrode 7 and one of the first electrode 5 and the second electrode 6. Positions of muscles and blood vessels are judged according to impedance detection, and then a direct current is connected between the first electrode 5 and the second electrode 6 during puncture to judge a tissue position punctured by the tip, thus realizing intelligent feedback of a syringe.

Figure 5:
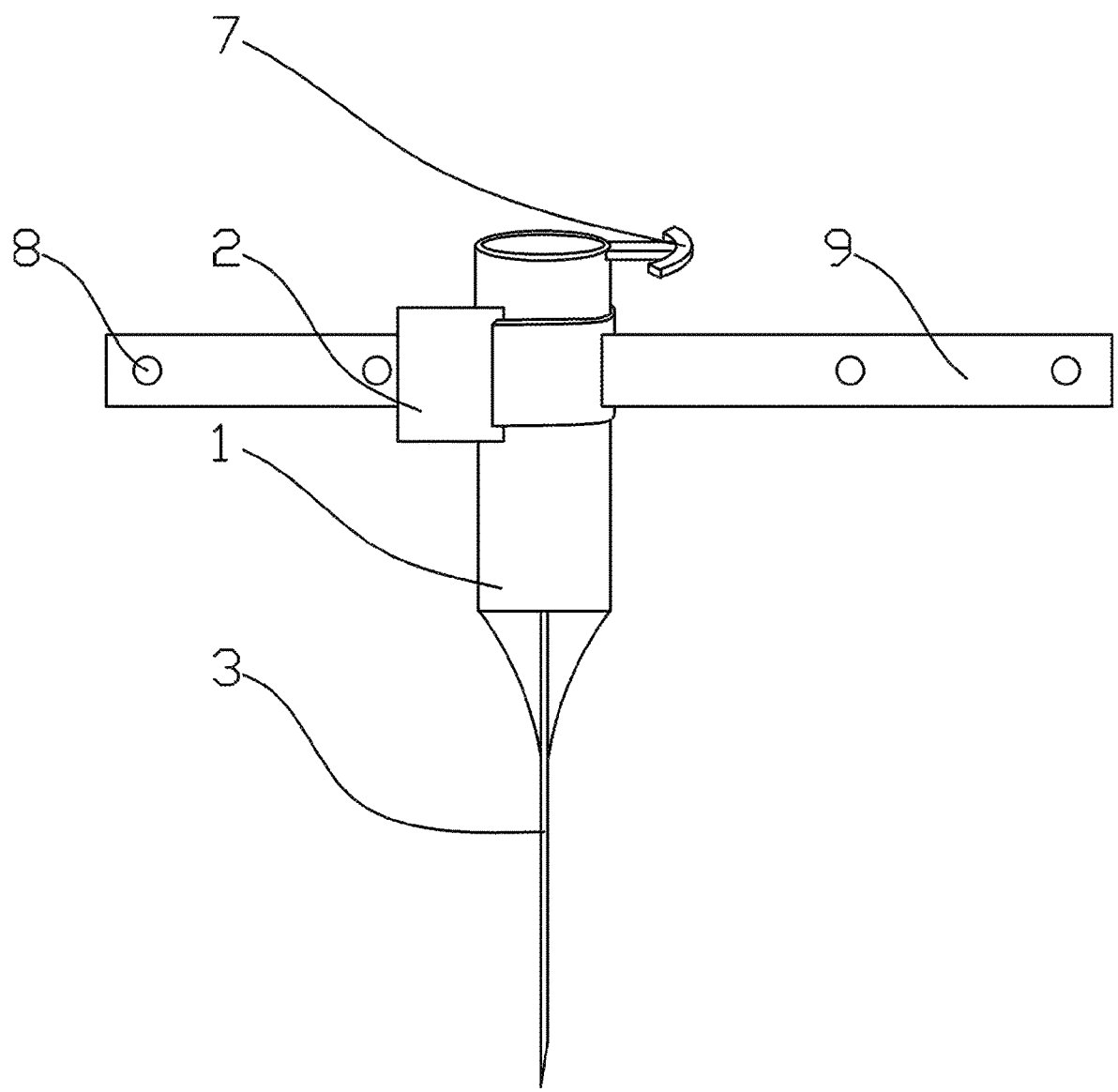
FIG. 5 is a schematic diagram of another preferred mechanism in the present invention.

Another preferred solution is shown in FIG. 5, the needle seat 1 is also provided with an array electrode 8, the array electrode 8 is electrically connected with the main control device 2 through the micro-signal amplification circuit, and the array electrode 8 and one of the first electrode 5 and the second electrode 6 form the frequency conversion impedance detection circuit. An alternating current is connected between the array electrode 8 and the first electrode 5 or the second electrode 6, and a position structure of a subcutaneous tissue is judged by impedance detection, such as positions of fat, body fluid, muscle, and blood vessel. Preferably, information of the position structure of the subcutaneous tissue is displayed by a displayer or a reminding device, and the displayer or the reminding device includes a display screen, an LED indicator light, or a buzzer. The information is displayed through the display screen, prompted through LED lights of different colors or brightnesses, or prompted through the buzzer. Then, the position of the tip on the human tissue is judged by the direct current applied between the first electrode 5 and the second electrode 6 during puncture. An accuracy of scanning detection can be further improved by using a structure of the array electrode 8, such as a scanning manner described in the Chinese patent document CN101564294A.

A preferred solution is shown in FIG. 5, a plurality of array electrodes 8 are provided, the plurality of array electrodes 8 are arranged on a flexible fixing belt 9, and the flexible fixing belt 9 is provided with an adhesive or a gluing buckle with ends connected with each other, so that the array electrodes 8 are able to reliably contact with the skin. An interference caused by poor contact between the array electrode 8 and the skin can be reduced by the solution.

In a preferred solution, a low frequency current signal of 0 Hz to 100 Hz is connected between the first electrode 5 and the second electrode 6 to determine a position of the tip of the syringe needle 3.

A medium and low frequency signal of 100 Hz to 50 k Hz is connected between one of the first electrode 5 and the second electrode 6, and the third electrode 7 or the array electrode 8 for scanning different tissues of a human body. A detection accuracy is further improved by using sensitivities of different tissues of the human body to currents with different frequencies. For example, the papers of Feng Fu, Yimin Zang, et al about measurement of a blood complex impedance frequency characteristic recorded that under conditions of 0.5 mA and a frequency of 100 Hz to 10 MHz, the position of the blood may be scanned on a body surface, and then the position of the blood vessel is judged.

A switching circuit is also provided for switching the low frequency current signal and the medium and low frequency signal. The switching circuit is preferably a soft switching circuit, which is namely a switching circuit controlled through software.

Embodiment 3

Figure 7:
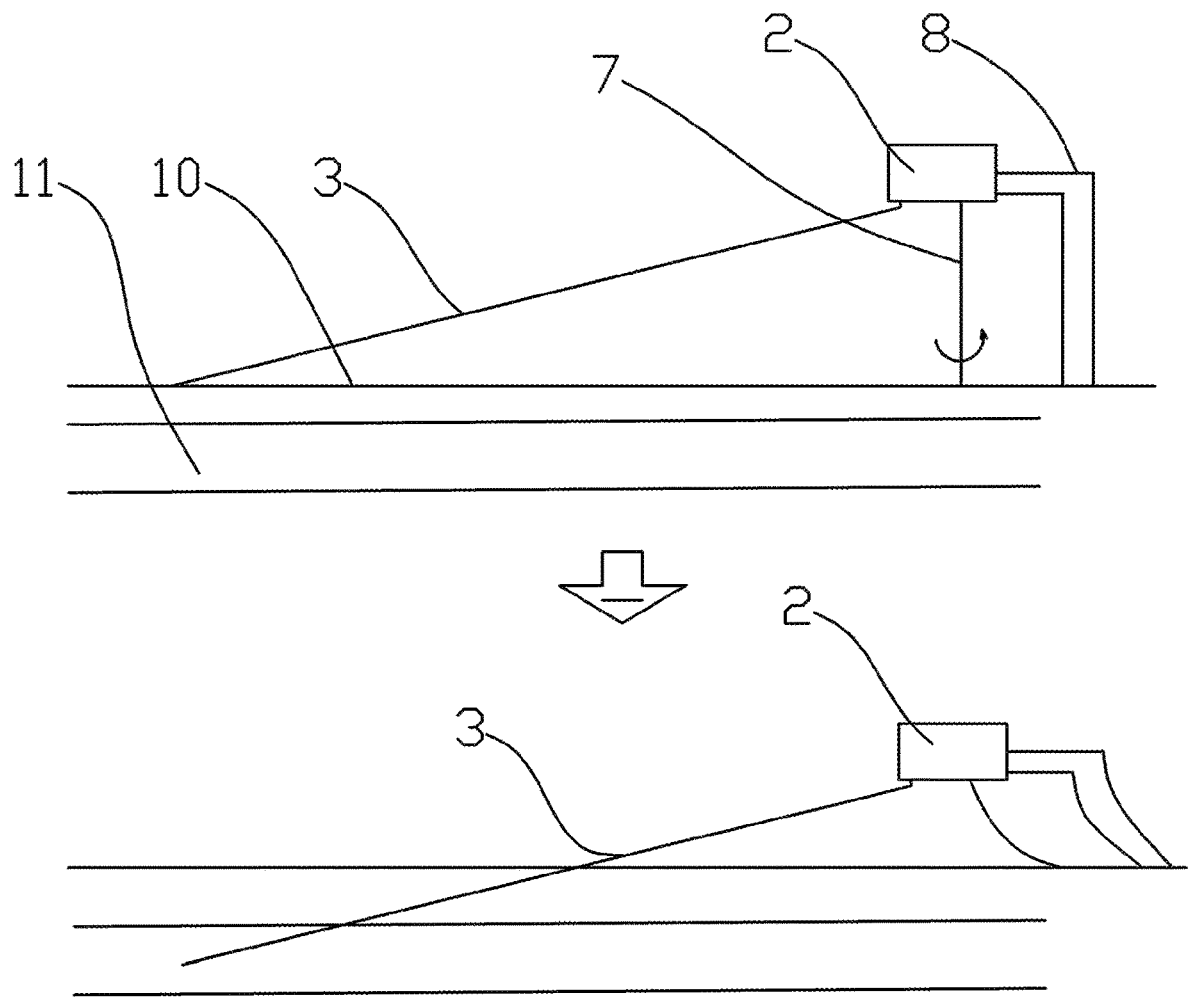
FIG. 7 is a schematic diagram of the present invention in use.
Figure 8:
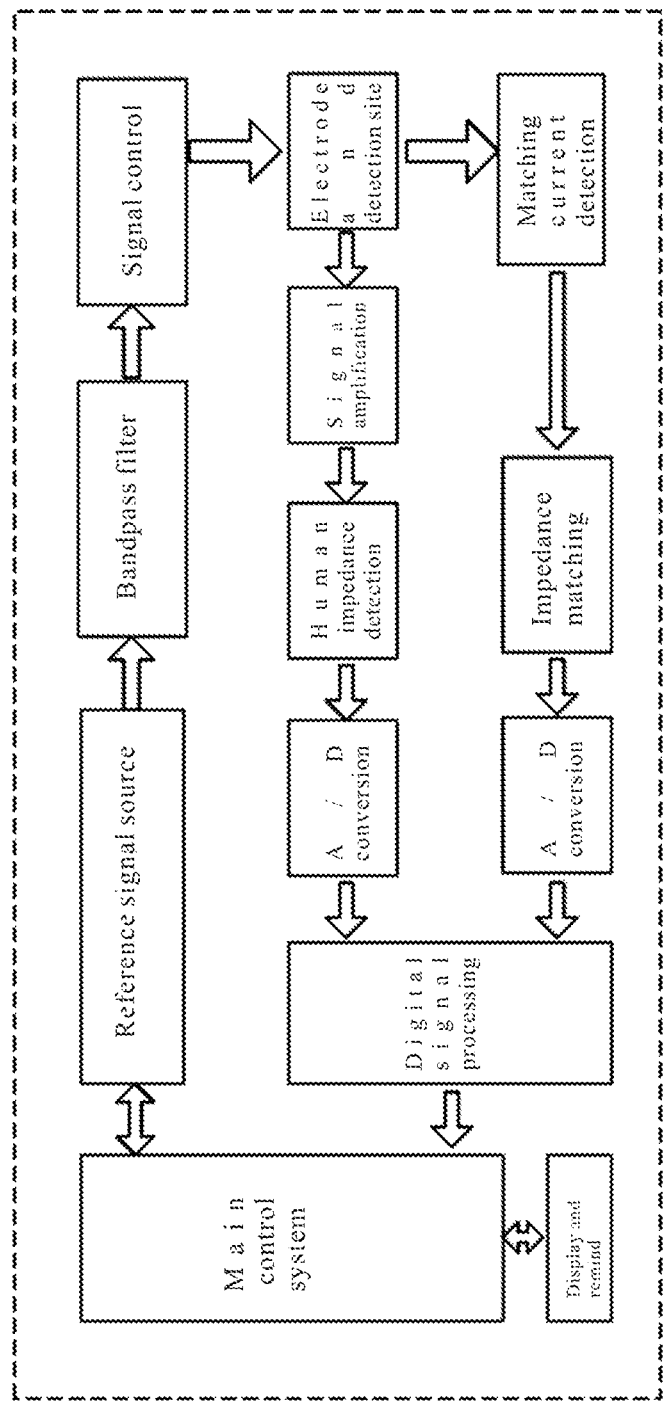
FIG. 8 is a frame diagram of a detection system of the present invention.

Based on the Embodiment 2, as shown in FIG. 7, arterial blood collection is taken as an example. The array electrode 8 is attached to skin 10 of a patient in use, and the third electrode 7 and the first electrode 5 also reliably contact with the skin. The main control system of the main control device 2 sends an instruction, and the reference signal source sends the alternating current. Preferably, the first electrode 5 sends the alternating current, with a frequency of 100 Hz to 50 k Hz. A direction of the syringe needle 3 is rotated along a surface of the skin with the third electrode 7 or the needle seat 1 as a center, thus ensuring reliable contact between the first electrode 5 and the skin during rotation. According to impedance detection, the positions of the muscles and the blood vessels are judged through images. After a target position is determined, the circuit is switched during puncture, the direct current is connected between the first electrode 5 and the second electrode 6, and tip puncture to the position of the human tissue is accurately judged by impedance, thus realizing the intelligent feedback of the syringe.

The above embodiments are only preferred technical solutions of the present invention, and shall not be regarded as limiting the present invention. The embodiments in the present application and the features in the embodiments can be arbitrarily combined with each other without conflict. The scope of protection of the present invention shall be the technical solutions recorded in the claims, including the equivalent alternatives of the technical features in the technical solutions recorded in the claims. Equivalent substitutions and improvements in the scope are also included in the scope of protection of the present invention.

What is claimed is:

1. A feedback-type intelligent syringe, comprising a syringe needle (3) and a needle seat (1), wherein
   the syringe needle (3) is provided with a first electrode (5) and a second electrode (6) for detecting impedance of a human tissue, the first electrode (5) and the second electrode (6) are electrically connected with a main control device (2), and the main control device (2) is electrically connected with a displayer or a reminding device, the syringe needle (3) is made of an insulating material or a metal material, and an outer layer of the syringe needle (3) is coated with an inner insulating layer (31),
   the first electrode (5) and the second electrode (6) are arranged along a length direction of the syringe needle (3),
   out layers of the first electrode (5) and the second electrode (6) are coated with outer insulating layers (12), and one end of the first electrode (5) and one end of the second electrode (6) are exposed only at positions close to a tip,
   a third electrode (7) is also arranged at a position of the needle seat (1), the third electrode (7) is used for reliable contact with skin, the third electrode (7) is electrically connected with the main control device (2) through a micro-signal amplification circuit, the third electrode (7) is rotatably connected with the needle seat (1), and the third electrode (7) and one of the first electrode (5) and the second electrode (6) form a frequency conversion impedance detection circuit,
   a signal generator configured to output a low frequency current signal of 0 Hz to 100 Hz between the first electrode (5) and the second electrode (6) to determine a position of the tip of the syringe needle (3),
   a signal generator configured to output a medium and low frequency signal of 100 Hz to 50k Hz between one of the first electrode (5) and the second electrode (6), and the third electrode (7) for scanning different tissues of a human body,
   in the main control device (2), a main control system is electrically connected with a reference signal source, the reference signal source is electrically connected with a band-pass filter, the band-pass filter is electrically connected with the micro-signal amplification circuit, and the micro-signal amplification circuit is electrically connected with the first electrode (5) and the second electrode (6),
   a current detection circuit (OP3) is electrically connected with the second electrode (6),
   a switching circuit is also provided for switching the low frequency current signal and the medium and low frequency signal, and
   the displayer or the reminding device comprises a display screen, an LED indicator light, or a buzzer,
   a structure of the main control device (2) is that: the main control system is electrically connected with the reference signal source, the reference signal source is electrically connected with the band-pass filter, and after the reference signal passes through the band-pass filter, a detection current is provided for the first electrode (5) and the second electrode (6) through a signal control module, and
   the first electrode (5) and the second electrode (6) are electrically connected with the micro-signal amplification circuit and the current detection circuit respectively, the micro-signal amplification circuit and the current detection circuit are electrically connected with at least two sets of A/D conversion modules respectively, the A/D conversion modules are electrically connected with a digital signal processing module, and the digital signal processing module is electrically connected with the main control system.

2. The feedback-type intelligent syringe according to claim 1, wherein,
   other end of the first electrode (5) and other end of the second electrode (6) extend to an outer wall of the needle seat (1), the main control device (2) is sleeved with the needle seat (1), an inner wall of the main control device (2) is provided with a first lead-in electrode (13) and a second lead-in electrode (14), and the first lead-in electrode (13) and the second lead-in electrode (14) are electrically connected with the first electrode (5) and the second electrode (6) respectively.

3. The feedback-type intelligent syringe according to claim 1, wherein
   the micro-signal amplification circuit is an instrument amplifier circuit.

4. The feedback-type intelligent syringe according to claim 1, wherein,
   the needle seat (1) is also provided with an array electrode (8), the array electrode (8) is electrically connected with the main control device (2) through the micro-signal amplification circuit, and the array electrode (8) and one of the first electrode (5) and the second electrode (6) form the frequency conversion impedance detection circuit.

5. The feedback-type intelligent syringe according to claim 4, wherein,
   a plurality of array electrodes (8) are provided, the plurality of array electrodes (8) are arranged on a flexible fixing belt (9), and the flexible fixing belt (9) is provided with an adhesive or a gluing buckle with ends connected with each other, so that the array electrodes (8) are able to reliably contact with the skin, and positions of muscles and blood vessels are judged outside the skin.

6. The feedback-type intelligent syringe according to claim 5, wherein,
   a signal generator configured to output a medium and low frequency signal of 100 Hz to 50k Hz between the array electrode (8) for scanning different tissues of a human body and one of the first electrode (5 and the second electrode (6).

7. The feedback-type intelligent syringe according to claim 4, wherein,
   a signal generator configured to output a medium and low frequency signal of 100 Hz to 50k Hz between the array electrode (8) for scanning different tissues of a human body and one of the first electrode (5) and the second electrode (6).

\* \* \* \* \*